Figure 1:
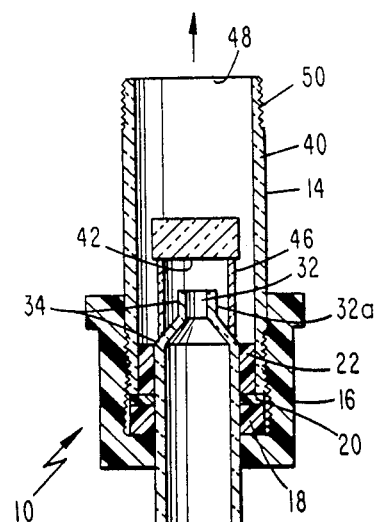
Figure 2:
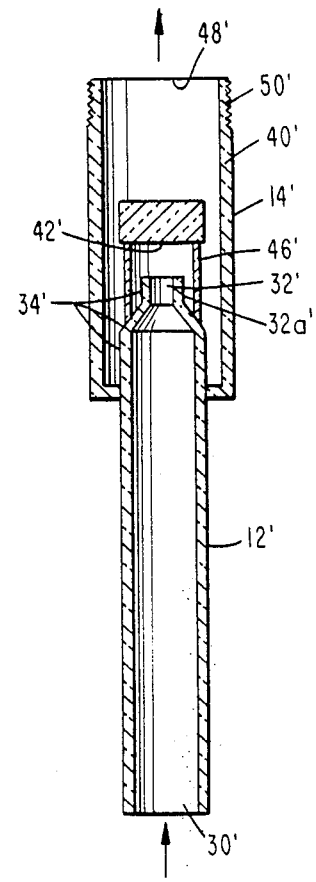
Figure 3:
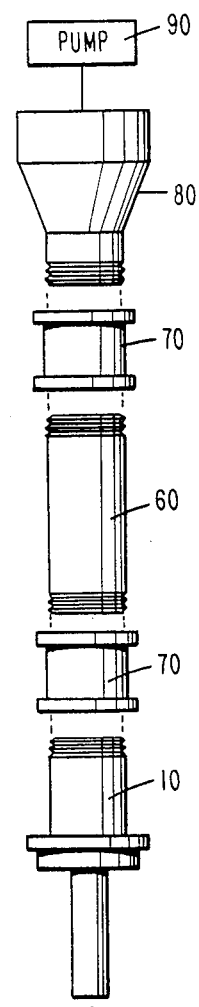

United States Patent [19]

Stevens et al.

[11] Patent Number: 4,961,966
[45] Date of Patent: Oct. 9, 1990

[54] FLUOROCARBON COATING METHOD

[75] Inventors: Robert K. Stevens, Raleigh; Charles Stone, Carrboro, both of N.C.

[73] Assignee: The United States of America as represented by the Administrator of the Environmental Protection Agency, Washington, D.C.

[21] Appl. No.: 477,390

[22] Filed: Feb. 9, 1990

Related U.S. Application Data

[62] Division of Ser. No. 201,242, May 25, 1988, Pat. No. 4,902,318.

[51] Int. Cl.$^5$ .................. B05D 1/36; B05D 3/02; B05D 7/00
[52] U.S. Cl. .................. 427/299; 427/327; 427/374.2; 427/379; 427/407.2; 427/409
[58] Field of Search .................. 427/299, 327, 374.2, 427/379, 407.2, 409

[56] References Cited

U.S. PATENT DOCUMENTS

| | | | |
|---|---|---|---|
| 4,620,995 | 11/1986 | Otomo et al. | 427/409 X |
| 4,789,565 | 12/1988 | Kon et al. | 427/409 X |
| 4,863,794 | 9/1989 | Fujii et al. | 427/407.2 X |

Primary Examiner—Michael Lusignan

[57] ABSTRACT

An inlet apparatus for gas-aerosol sampling comprises an elutriator column and an impactor member. The elutriator column comprises an inlet and an impact accelerator jet outlet, and the inner surface of the column is provided with a coating of polytetrafluoroethylene-containing polymer. The impactor member includes a housing which surrounds the impact accelerator jet outlet and an impactor surface arranged within the housing and opposite the impact accelerator jet outlet. The inner surface of the housing is also provided with a polytetrafluoroethylene-containing polymer coating.

2 Claims, 1 Drawing Sheet

FLUOROCARBON COATING METHOD

This is a division, of application Ser. No. 07/201,242, now U.S. Pat. No. 4,902,318, patented Feb. 20, 1990.

FIELD OF THE INVENTION

The present invention relates to an inlet apparatus for use in gas-aerosol sampling. More particularly, the present invention relates to an inlet apparatus for use in gas-aerosol sampling wherein removal of larger size particles, for example, particles having a size greater than about 3 μm in diameter, is desired while retaining smaller size particles and gases which are contained in a sample.

BACKGROUND OF THE INVENTION

Over the past several years, various studies have been conducted to measure the levels of toxic and related air pollutants in many different geographical areas. For example, a number of investigations have been made to measure ambient concentrations of $HNO_3$, $SO_2$, nitrates and sulfates which contribute to acidic deposition and acid rain phenomena in the environment. In order to increase the accuracy of these types of measurements, more precise sampling and analysis apparatus and procedures have been developed for measuring ambient concentrations of the aforementioned chemicals. For example, filter packs consisting of an inert filter followed by a treated filter have been developed to provide apparently reliable data for measuring sulfates and $SO_2$.

However, measurement of $HNO_3$ and nitrate compounds has proven to be very difficult owing to losses of $HNO_3$ in the sampling systems, for example, in the inlet portions of the sampling apparatus, and owing to the difficulty in differentiating vapor phase $HNO_3$ from $HNO_3$ produced from the dissociation of $NH_4NO_3$ during sampling procedures. The use of one or more annular denuders connected in series has been proposed by Possanzini et al, *Atmos. Environ.*, 17, 2605 (1983), for sampling ambient concentrations of $HNO_3$. The denuders are treated with chemicals such as sodium carbonate and citric acid so that most of the gaseous acids and bases can be absorbed onto the denuders. This allows the particles to pass through the denuders without undergoing chemical transformations or being deposited on the denuder surfaces by diffusion. However, it appears that the presence of larger particles in a sample effects the efficiency of the denuders owing to the difficulty in sampling and quantifying the larger particle fraction, particle re-entrainment and volatilization of large particle chemical components. Accordingly, there is a need for a means which separates larger size particles from the sample while retaining smaller size particles and gaseous components of the sample.

SUMMARY OF THE INVENTION

It is therefore an object of the present invention to provide an inlet apparatus for gas-aerosol sampling and, more particularly, to provide an inlet apparatus for gas-aerosol sampling which effects removal of larger size particles from a sample while retaining smaller size particles and gaseous components in the sample. It is an additional object of the invention to provide an inlet apparatus which provides improved sampling of ambient concentrations of toxic air pollutants such as $HNO_3$. It is an additional object of the invention to provide an inlet apparatus for gas-aerosol sampling which may be used in combination with filter means and/or denuder apparatus presently employed in the sampling art.

These and additional objects and advantages are provided by the inlet apparatus for gas-aerosol sampling according to the present invention which comprises an elutriator column and an impactor member. The elutriator column has an inlet at one end for admitting a gas-aerosol sample and an impact accelerator jet outlet at the other end. The impactor member is connected with the elutriator column and includes a housing which surrounds the impactor accelerator jet outlet of the elutriator column. The impactor member further includes an impactor surface arranged within the housing and opposite the impact accelerator jet outlet whereby the impact accelerator jet outlet delivers the gas-aerosol sample to the impactor surface to achieve separation of larger size particles from the gas-aerosol sample. The inner surface of the elutriator column and the inner surface of the housing are provided with a coating of polytetrafluoroethylene-containing polymer. The coating renders the inlet apparatus inert and prevents smaller size particles or gaseous components of a sample from being retained therein while separation of larger size particles is effected by the impact aerosol jet outlet in combination with the impactor surface. The inlet apparatus therefore provides improved sampling of gas-aerosol samples.

These and additional objects and advantages of the present invention will become more apparent in view of the following detailed description.

BRIEF DESCRIPTION OF THE DRAWING

The inlet apparatus of the present invention will be more fully understood in view of the drawing in which:

FIG. 1 represents a cross-sectional view of a first embodiment of the inlet apparatus of the invention;

FIG. 2 represents a cross-sectional view of a second embodiment of the inlet apparatus of the invention; and FIG. 3 is a front exploded view of the inlet apparatus according to the present invention arranged for use in connection with a conventional denuder and filter means comprising a filter pack.

DETAILED DESCRIPTION

The inlet apparatus of the present invention is particularly adapted for gas-aerosol sampling wherein removal of larger size particles is desired while retaining smaller size particles and gaseous components in the sample. While the size of the larger particles which are removed in the inlet apparatus of the present invention will depend on the dimensions of the apparatus, the inlet apparatus is particularly useful for removing particles having a size larger than about 5 μm in diameter, and more particularly, greater than about 3 μm in diameter, from gas-aerosol samples. These larger size particles are removed while smaller size particles and gaseous components contained in the sample are retained.

The inlet apparatus includes an elutriator column and an impact member connected with the elutriator column. With reference to FIG. 1, the inlet apparatus 10 includes the elutriator column 12 and the impactor member 14. The elutriator column and the impact member may be formed of various materials including, but not limited to, glass, aluminum and stainless steel. In a preferred embodiment, the elutriator column and the impactor member are formed of glass. Suitable means may be included in the inlet apparatus for connecting the elutriator column with the impactor member in a sealed relation. For example, as shown in FIG. 1, a cap member 16 and sealing rings 18,20,22 may be provided for connecting the elutriator column and the impactor member in sealed relation.

The elutriator column 12 has an inlet 30 at its one end and an impactor accelerator jet outlet 32 at its other end. A gas-aerosol sample is admitted to the elutriator column through the inlet and is accelerated from the column through the impact accelerator jet outlet. The outlet is preferably provided with a nozzle portion 32*a* as shown in FIG. 1, which nozzle portion has a diameter less than the diameter of the remainder of the elutriator column. Although the dimensions of the impact accelerator jet outlet may vary depending on the environment which is to be sampled, for example, depending on the flow rate and the size of the particles which are to be excluded by the impactor, for sampling $HNO_3$ containing environments it is preferred that the diameter of the impact accelerator jet outlet is in the range of about 0.5 mm to about 10 mm, and more preferably, less than about 5 mm. It is also preferred that the length of the nozzle portion is less than about 10 mm.

Additionally, the diameter of the elutriator column is preferably sufficiently small to prevent the entry of exceptionally large particles, for example, particles which are greater than about 10 mm in diameter.

The impact member 14 which is connected with the elutriator column includes a housing 40 and an impactor surface 42. As shown in FIG. 1, the housing 40 surrounds the impact accelerator jet outlet of the elutriator column and the impactor surface 42 is arranged within the housing and opposite the impact accelerator jet outlet. The impact accelerator jet outlet delivers the gas-aerosol sample to the impactor surface in order to achieve separation of the larger size particles from the gas-aerosol sample. The larger size particles are retained on the impactor surface. The distance between the impactor surface and the impact accelerator jet outlet may, as with the diameter of the jet outlet, be varied depending on the environment in which the inlet apparatus is to be used. It is preferred however that the distance between the impactor surface and the jet outlet is less than about 20 mm, and more preferably, less than about 10 mm when the inlet apparatus is to be employed for use in an environment containing $HNO_3$ gaseous component. The impactor surface is supported opposite the impact accelerator jet outlet by any suitable means including, as shown in FIG. 1, supporting members 46 extending upwardly from the outer surface of the elutriator column.

The impactor surface preferably comprises a flat surface which supports a removable membrane filter (for example, Whatman quartz filter material) or preferably comprises a removable porous disc. The impactor surface may be formed of various materials including glass, ceramics or metals, for example, stainless steel, aluminum or the like. Additionally, it is preferred that the impactor surface, and membrane filter if included, is coated with a coating material to increase retention of the larger particles thereon. Suitable coating materials include silicone grease, stopcock grease and mineral oil. The capacity of the coated impactor surface to retain particles generally influences the impactor removal efficiency.

In accordance with an important feature of the invention, both the inner surface of the elutriator column and the inner surface of the impactor member housing are provided with a coating of a polytetrafluoroethylene-containing polymer. Preferably, the outer surfaces of the elutriator column which are housed within the impact member housing are also provided with a coating of polytetrafluoroethylene-containing polymer. These surfaces are indicated at 34 in FIG. 1. The coating renders the surfaces inert and prevents retention in the inlet apparatus of smaller size particles and/or gases contained in the sample. Thus, the smaller size particles and gases contained in the sample are retained in the sample as the sample passes through the inlet apparatus. Thus, while larger size particles are removed by means of the impact jet accelerator outlet and the impact surface, smaller size particles and gases are retained in the sample.

Moreover, the method which is preferably employed for producing the polytetrafluoroethylene-containing polymer coatings according to the present invention provides improved inert surfaces in the inlet apparatus. The method which is used to provide the coatings comprises first roughing the surfaces which are to be coated in order to provide a surface which is receptive to a polymer coating. The roughened surface is then first coated with a primer polytetrafluoroethylene monomer mixture. The resulting coating is dried and heated to a temperature of about 250° C. Once the coating has cooled, a second monomer mixture of fluorinated ethylene-propylene monomers is applied. The coated surfaces are then heated to about 350° C. to effect polymerization and crosslinking of the coating. The resultant polytetrafluoroethylene-containing polymer coating provides an inert smooth surface which does not retain small particles and/or gaseous components when used in an inlet apparatus as described according to the present invention.

As shown in FIG. 2, the inlet apparatus 10' of the invention may be formed as one piece wherein the elutriator column 12' and the impactor member 14' are formed and connected as an integral one piece unit. Portions of the inlet apparatus of FIG. 2 which correspond with portions of the inlet apparatus shown in FIG. 1 are similarly numbered with the additional "'" designation.

As shown in both FIGS. 1 and 2, the impactor member housing includes an outlet 48 or 48' for delivering the gas-aerosol sample to additional sampling apparatus which is conventionally used in the art. For example, as shown in FIG. 3, the inlet apparatus 10 or 10' may be connected in series with one or more denuders 60 and/or a conventional filter pack 80 known in the art. The impactor member housing 40 is provided with means such as screw threads 50 at its end adjacent the outlet 48 for attaching the inlet apparatus with a denuder, a filter pack or the like. The inlet apparatus, the denuders and the filter pack may be coupled together with conventional screw-type couplers 70 also shown in FIG. 3. The flow of a sample through the inlet apparatus, the one or more denuders and the filter pack may be established by arrangement of the assembly within a flowing stream or by the use of a suitable pump means 90 shown schematically in FIG. 3. Alternatively, the inlet apparatus may be connected with a filter member such as a filter pack, without any denuder therebetween, when the direct collection of fine particles is desired. The inlet apparatus according to the present invention is particularly suitable for use with flow rates of between 1 and 20 liters per minute for the separation of fine and coarse particles.

The inlet apparatus of the invention is additionally advantageous in that it is generally less expensive than commercially available devices. Additionally, the inlet apparatus allows for recovery of large particles for subsequent analysis if desired. The coupling of the elutriator column with the impactor member achieves sharp non-contaminating separation of large and small particles while the coating on the inner surfaces of the elutriator column and the housing of the impactor member provides little if any loss of reactive gases to the internal wall surfaces of the inlet apparatus. Additionally, the inlet apparatus may be used as a preseparator means for removing coarse particles from a sample and allowing collection of fine particles on a filter means located downstream of the inlet apparatus.

The novel features of the present invention will be more fully understood in view of the following examples which are offered to illustrate but not limit the scope of the present invention.

EXAMPLE 1

This example demonstrates the use of the inlet apparatus of the present invention in separating large particles from a particle containing sample. Two inlet apparatus were tested, each of which had a structure as shown in FIG. 1. The first apparatus comprised a glass elutriator column and a glass impact member housing. The impact accelerator jet diameter of the first apparatus was measured to be 3.2 mm and the distance between the jet outlet and the impact surface was measured to be 6.0 mm. The impact surface comprised a glass disk formed with a recession which accommodated a 13 mm diameter membrane filter disk. The recessed portion was coated with a high vacuum silicone grease, and the filter disk was impregnated with the silicone grease and arranged in the recession to form a smooth impact surface. The application of the silicone grease was effected using a syringe and a toluene-silicone grease solution. With reference to FIG. 1 a plastic screw cap 16, a neoprene washer 18, a teflon washer 20 and a teflon bushing 22 were used to sealingly connect the impactor member and the elutriator column. The second inlet apparatus which was tested was similar to the first apparatus except that the jet outlet diameter of the second apparatus was 4.0 mm and the impact surface comprised a flat glass disk. Tests 1–10 on the second apparatus were performed using a noncoated impact surface in apparatus while tests 11–14 on the second apparatus were conducted using the impactor surface coated with a toluene-silicone grease solution.

The testings of the inlet apparatus were performed using a wind tunnel. Flow rates through the first apparatus varied from 15.7 to 16.7 LPM while the flow rates through the second apparatus were 16.7 LPM. A teflon filter holder with a 0.8 μm pore size membrane filter was attached in-line to back up each inlet apparatus. The test particles were generated from a sodium fluorescein (uranine) dye solution using a Berglund-Liu monodisperse aerosol generator equipped with a Krypton-85 charge neutralizer. The size and shape uniformity of the generated aerosol particles were verified using a scanning electron microscope (SEM). Samples for the SEM observations were collected on a 1.0 μm pore size teflon filter placed adjacent the inlet of the elutriator column. Particles with aerodynamic diameters of 0.8, 1.9, 2.8 and 4.0 μm were generated during the testing of the first apparatus and particles with aerodynamic diameters of 1.1, 2.0, 2.5, 4.3 and 6.3 μm were generated during the testing of the second apparatus.

After each test, the inlet apparatus was removed to determine its collection performance, the results of which are set forth in Tables I and II.

TABLE I

MASS COLLECTION PERFORMANCE
(3.2 mm jet outlet diameter)

| Test No. | $D_{AE}$ μm | MASS FRACTION COLLECTED, % Impaction Disc: Surface | Impaction Disc: Embedded | Wall Loss | E, Impactor Subtotal[A] | Backup Filter | Net Total System | Inlet Loss |
|---|---|---|---|---|---|---|---|---|
| 1 | 1.9 | 88 | 0 | 1 | 89 | 11 | 100 | 0 |
| 2 | 1.9 | 43 | 1 | 1 | 45 | 55 | 100 | 0 |
| 3 | 4.0 | 82 | 2 | 2 | 86 | 14 | 100 | 0.6 |
| 4 | 4.0 | 88 | 5 | 1 | 94 | 6 | 100 | 1.0 |
| 5 | 4.0 | 93 | 1 | 0 | 94 | 6 | 100 | 1.4 |
| 6 | 0.8 | 0 | 0 | 0 | 0 | 100 | 100 | 0 |
| 7 | 0.8 | 0 | 0 | 0 | 0 | 100 | 100 | 0 |
| 8 | 1.9 | 58 | 3 | 1 | 62 | 38 | 100 | 0 |
| 9 | 1.9 | 65 | 1 | 1 | 67 | 33 | 100 | 1.9[C] |
| 10 | 2.8 | 86 | 1 | 0 | 87 | 13 | 100 | 0.7 |
| 11 | 2.8 | 85 | 1 | 1 | 87 | 13 | 100 | 0.5 |
| 12 | 2.8 | 92 | <1 | 0 | 92 | 8 | 100 | 0.6 |

A = E% = (Impaction Disc Mass + Wall Loss Mass) + Net Total System Mass.
B = % Inlet Loss = Inlet Mass + (Inlet Mass + Net Total System Mass).
C = Apparent outlier.

TABLE II

MASS COLLECTION PERFORMANCE
(4 mm jet outlet diameter)

| Test No. | $D_{AE}$ μm | MASS FRACTION COLLECTED, % Impaction Disc: Surface | Impaction Disc: Embedded | Wall Loss | E, Impactor Subtotal[A] | Backup Filter | Net Total System | Inlet Loss[B] |
|---|---|---|---|---|---|---|---|---|
| 1 | 2.5 | 38 | NA | 15 | 53 | 47 | 100 | 0 |
| 2 | 2.5 | 15 | NA | 11 | 26 | 74 | 100 | 0 |
| 3 | 4.3 | 62 | NA | 18 | 80 | 20 | 100 | 0 |
| 4 | 4.3 | 45 | NA | 27 | 72 | 28 | 100 | 0 |
| 5 | 6.3 | 20 | NA | 54 | 74 | 26 | 100 | 3 |
| 6 | 6.3 | 44 | NA | 31 | 75 | 25 | 100 | 1 |
| 7 | 2.0 | 11 | NA | 6 | 17 | 83 | 100 | 0 |

TABLE II-continued

MASS COLLECTION PERFORMANCE
(4 mm jet outlet diameter)
MASS FRACTION COLLECTED, %

| Test No. | $D_{AE}$ μm | Impaction Disc: Surface | Impaction Disc: Embedded | Wall Loss | E, Impactor Subtotal[A] | Backup Filter | Net Total System | Inlet Loss[B] |
|---|---|---|---|---|---|---|---|---|
| 8 | 2.0 | 10 | NA | 5 | 15 | 85 | 100 | 0 |
| 9 | 1.1 | 0 | NA | 0 | 0 | 100 | 100 | 0 |
| 10 | 1.1 | 0 | NA | 0 | 0 | 100 | 100 | 0 |
| 11[C] | 2.5 | 87 | 7 | 1 | 95 | 5 | 100 | 0 |
| 12[C] | 2.5 | 92 | 4 | 1 | 97 | 3 | 100 | 0 |
| 13[D] | 2.5 | 82 | 16 | 0 | 98 | 2 | 100 | 0 |
| 14[D,E] | 2.5 | 60 | 6 | 5 | 71 | 29 | 100 | 0 |

A = E% = (Impaction Disc Mass + Wall Loss Mass) ÷ Net Total System.
B = % Inlet Loss = Inlet Mass ÷ (Inlet Mass + Net System Total Mass).
C = 0.04 mL of Toluene-silicone applied to impaction surface.
D = 0.08 mL of Toluene-silicone applied to impaction surface.
E = Test No. 14 results affected by uneven coating media. Particle bounce.
NA = Not applicable. Impaction disc uncoated.

The results set forth in Tables I and II demonstrate that both of the inlet apparatus provided a sharp particle cut point for separating larger size particles from smaller size particles.

EXAMPLE 2

This example demonstrates the use of the inlet apparatus of the present invention for sampling an environment containing $HNO_3$ gaseous component. The inlet apparatus was a type as set forth in FIG. 1 comprising a glass elutriator column and a glass impactor member. Nitric acid was generated using a Unisearch Associates permeatation tube maintained at 53° C. The acid was diluted to a total volume of 7 cfm with purified ambient air. The inlet apparatus was attached to a cylindrical sampling manifold of the device. Additionally, a 47 mm Nuclepore open-face holder and nylon filter were attached at the downstream outlet of the impactor member housing. Additionally, an open-face nylon control filter was directly attached to a sampling manifold port of the device. The flow rate through the inlet apparatus of the present invention was approximately 16 LPM. The control filter was tested at a flow rate of 10 lpm and at a flow rate of 20 lpm. Three measurements on each device were performed at about 50% relative humidity and 20° C. to simulate day conditions and at about 80% relative humidity and 13° C. to simulate night conditions. The second and third measurements were done immediately following filter changes and reflect the effects of conditioning from preceding trials. The nylon filters were extracted in an ion chromatography eluent solution comprising 2.7 mM $HCO_3^-$—2.1 Mm $CO_3^-$ and, together with washings, analyzed by ion chromatography for nitrate. The results of these measurements are set forth in Table III.

TABLE III $HNO_3$ TRANSMISSION EFFICIENCY

| | 50% RH, 21° C. | | | 80% RH, 13° C. | | |
|---|---|---|---|---|---|---|
| | A | B | C | A | B | C |
| Inlet Assembly of Invention, % | 104 | 102 | 114 | 81.2 | 80.5 | 75.1 |

TABLE III-continued $HNO_3$ TRANSMISSION EFFICIENCY

| | 50% RH, 21° C. | | | 80% RH, 13° C. | | |
|---|---|---|---|---|---|---|
| Control, ug/m³ | | | | | | |
| 10 lpm | 9.07 | 9.66 | 11.1 | *7.98 | 5.45 | 4.17 |
| 20 lpm | 9.90 | 11.0 | 11.2 | 6.22 | 5.48 | 4.17 |

*suspect result; not used for calculation

The $HNO_3$ transmission efficiency was evaluated relative to the $HNO_3$ sampled with the control filter. At about 50% relative humidity, the $HNO_3$ measured with the control filter at 10 lpm were about 10% lower than those at 20 lpm, suggesting greater wall losses in the sampling manifold port. At 80% relative humidity, no significant difference was measured in the $HNO_3$ concentrations at the two flow rates. The results set forth in Table III demonstrate that the inner surfaces of the inlet assembly according to the present invention are inert and do not retain any of the gaseous $HNO_3$ contained in the gas samples. Thus, the inlet apparatus according to the present invention is particularly advantageous for use in sampling gas-aerosol samples containing gaseous $HNO_3$.

The preceding examples are set forth to illustrate specific embodiments of the invention and are not intended to limit the scope of the compositions and methods of the present invention. Additional embodiments and advantages within the scope of the claimed invention will be apparent to one of ordinary skill in the art.

What is claimed is:

1. A method for providing a polytetrafluoroethylene coating on a surface, comprising roughing the respective surfaces, coating the roughened surfaces with polytetrafluoroethylene monomers, drying and heating the resulting coating to a temperature of about 250° C. followed by cooling, and coating the resulting surfaces with fluorinated ethylene-propylene monomers followed by heating to a temperature of about 350° C. to effect polymerization and crosslinking.

2. A method for providing a polytetrafluoroethylene coating on a surface as defined by claim 1, wherein the surface is formed of a material selected from the group consisting of glass, aluminum and stainless steel.

* * * * *